United States Patent
Illidge et al.

(10) Patent No.: US 10,626,143 B2
(45) Date of Patent: Apr. 21, 2020

(54) METHOD OF PROTEIN MANUFACTURE

(71) Applicant: UCB BIOPHARMA SPRL, Brussels (BE)

(72) Inventors: Christopher Mark Illidge, Slough (GB); Neil Alan Watson, Slough (GB)

(73) Assignee: UCB BIOPHARMA SPRL, Brussels (BE)

( * ) Notice: Subject to any disclaimer, the term of this patent is extended or adjusted under 35 U.S.C. 154(b) by 93 days.

(21) Appl. No.: 15/538,282

(22) PCT Filed: Dec. 18, 2015

(86) PCT No.: PCT/EP2015/080526
§ 371 (c)(1),
(2) Date: Jun. 21, 2017

(87) PCT Pub. No.: WO2016/102378
PCT Pub. Date: Jun. 30, 2016

(65) Prior Publication Data
US 2017/0342105 A1 Nov. 30, 2017

(30) Foreign Application Priority Data
Dec. 22, 2014 (EP) .................................... 14199722

(51) Int. Cl.
| | |
|---|---|
| *C07K 1/36* | (2006.01) |
| *C07K 1/113* | (2006.01) |
| *C07K 1/18* | (2006.01) |
| *C07K 14/705* | (2006.01) |
| *C07K 16/24* | (2006.01) |
| *C12N 5/00* | (2006.01) |
| *C12N 15/74* | (2006.01) |
| *C12N 15/79* | (2006.01) |
| *C12P 21/02* | (2006.01) |

(52) U.S. Cl.
CPC .............. *C07K 1/36* (2013.01); *C07K 1/1133* (2013.01); *C07K 1/18* (2013.01); *C07K 14/705* (2013.01); *C07K 16/241* (2013.01); *C12N 5/0018* (2013.01); *C12N 15/74* (2013.01); *C12N 15/79* (2013.01); *C12P 21/02* (2013.01); *C12N 2500/50* (2013.01); *C12N 2501/20* (2013.01)

(58) Field of Classification Search
None
See application file for complete search history.

(56) References Cited

U.S. PATENT DOCUMENTS

| | | |
|---|---|---|
| 5,665,866 A | 9/1997 | Weir et al. |
| 8,969,036 B2 | 3/2015 | Sehdev et al. |
| 9,309,280 B2 | 4/2016 | Spitali et al. |
| 9,751,930 B2 | 9/2017 | Wild |
| 10,189,897 B2 | 1/2019 | Spitali et al. |
| 2008/0003644 A1 | 1/2008 | Sehdev et al. |
| 2013/0060009 A1 | 3/2013 | Bilgischer et al. |
| 2013/0178607 A1 | 7/2013 | Wild |
| 2013/0184439 A1 | 7/2013 | Spitali et al. |
| 2013/0273607 A1 | 10/2013 | O'Connor |
| 2016/0108119 A1 | 4/2016 | Spitali et al. |
| 2018/0117153 A1 | 5/2018 | Heywood et al. |
| 2019/0135909 A1 | 5/2019 | Spitali et al. |

FOREIGN PATENT DOCUMENTS

| | | | |
|---|---|---|---|
| JP | 2013-522252 | 6/2013 | |
| WO | WO-0055183 A1 * | 9/2000 | ............... B82Y 5/00 |
| WO | WO-2006047340 A2 * | 5/2006 | ....... A61K 39/39525 |
| WO | WO-2006060083 A1 * | 6/2006 | ........... C07K 1/1133 |
| WO | WO 2007/003898 | 1/2007 | |
| WO | WO 2008/008975 | 1/2008 | |
| WO | WO 2008/076933 | 6/2008 | |
| WO | WO 2011/113601 | 9/2011 | |
| WO | WO 2016/102383 | 6/2016 | |

OTHER PUBLICATIONS

Chapman, A. P. "PEGylated antibodies and antibody fragments for improved therapy: a review" *Advanced Drug Delivery Reviews*, Jun. 17, 2002, pp. 531-545, vol. 54, No. 4.

Humphreys, D. P. et al. "Alternative antibody Fab' fragment PEGylation strategies: combination of strong reducing agents, disruption of the interchain disulphide bond and disulphide engineering" *Protein Engineering, Design & Selection*, May 1, 2007, pp. 227-234, vol. 20, No. 5.

Roberts, M. J. et al. "Chemistry for peptide and protein PEGylation" *Advanced Drug Delivery Reviews*, Jun. 17, 2002, pp. 459-476, vol. 54, No. 4.

Wang, C. et al. "High Recovery Refolding of rhG-CSF from *Escherichia coli*, Using Urea Gradient Size Exclusion Chromatography" *Biotechnology Progress*, Feb. 1, 2008, pp. 209-213, vol. 24, No. 1.

Written Opinion in International Application No. PCT/EP2015/080526, dated Feb. 19, 2016, pp. 1-5.

\* cited by examiner

*Primary Examiner* — Daniel E Kolker
*Assistant Examiner* — James L Rogers
(74) *Attorney, Agent, or Firm* — Saliwanchik, Lloyd & Eisenschenk (57) ABSTRACT

The present invention provides a novel method for manufacturing a protein, particularly where said protein is to be coupled with another molecule. The invention further provides a method for industrial scale protein manufacturing to obtain proteins, e.g., for therapeutic purposes.

12 Claims, 3 Drawing Sheets

METHOD OF PROTEIN MANUFACTURE

CROSS-REFERENCE TO RELATED APPLICATION

This application is the U.S. national stage application of International Patent Application No. PCT/EP2015/080526, filed Dec. 18, 2015.

FIELD OF THE INVENTION

The present invention belongs to the field of protein purification. More specifically, it relates to a process for the purification of antibodies and antibody fragments.

BACKGROUND OF THE INVENTION

In the field of therapeutics the use of proteins and antibodies and antibody-derived molecules in particular has been constantly gaining presence and importance, and, consequently, the need for controlled manufacturing processes has developed in parallel. The commercialization of therapeutic proteins requires they are produced in large amounts. For this purpose the protein is frequently expressed in a host cell and subsequently be recovered and purified, prior to its preparation into an administrable form.

Depending on the protein to be expressed the choice of host cell may be a mammalian host cell, frequently a CHO (Chinese hamster ovary) cell, or a bacterial host cell. In the first case, the protein is typically secreted into the culture supernatant which is recovered, and the solution is then processed for protein purification.

When the host cell is a Gram negative prokaryotic cell, an often preferred expression system involves the newly synthesized protein accumulating within and being isolated from the periplasmic space. In this case, once the desired level of protein expression has been achieved, it is the cells that are harvested and processed. The protein is then recovered by means of subjecting the harvested cells to a protein extraction process which involves releasing the protein from the periplasm into solution and subsequent removal of cell debris and other impurities. These steps of cell harvest to protein release are typically included in what is termed primary recovery. The resulting protein-containing solution is then processed for protein purification. Preferred Gram negative prokaryotic cells used for periplasmic expression are generally *Escherichia coli* strains or *Pseudomonas fluorescens* cells.

Protein purification from complex mixtures is adapted to the target protein. In the case of antibodies and antibody-derived products, purification typically involves a first product capture step via chromatography which offers a first purification and significant concentration of the product. This first step is usually followed by one or more further chromatographic steps used to reduce contaminants such as host cell impurities, medium, purification process-related impurities and product-related impurities.

In recent years it has become increasingly common for different proteins, including antibodies and antibody derived fragments, to be coupled to another molecule with a particular function, this is applied both to diagnostic and therapeutic uses, to name but a few examples it may be to target the antibody to a particular set of cells, alternatively it may be a drug which is targeted by the antibody to its specific site of action, or the molecule may be destined to increase the antibody's half-life in an animal. The latter is particularly the case regarding antigen binding antibody fragments which tend to be rapidly cleared from the circulation of animals.

Different molecules can be coupled to a protein via a reactive group in the protein which either occurs naturally in the protein or is artificially introduced by protein engineering. Frequently, favoured reactive groups for protein binding to a second molecule are thiol groups present in unpaired cysteine residues. In this sense, antibody hinges are common regions for site specific reaction since they contain cysteine residues and are remote from other regions of the antibody likely to be involved in antigen binding. For example, reaction with polyethylene glycol (PEG) or PEGylation of thiol groups is a well-known approach to site-specific PEGylation, where a variety of thiol-specific reagents are available.

However, in native proteins, cysteine residues are usually involved in disulfide bridges or responsible for interaction with metals or other proteins. Therefore, in order to achieve site-specific binding, these reactive groups need to be in the correct conformation, i.e. their thiol groups being free, so as to enable their reaction. For example, PEGylation of G-CSF at a single cysteine residue was described in Veronese et al. Bioconjugate Chemistry 2007 November-December; 18(6): 1824-30 whereby the PEGylation was performed under transient denaturing conditions. There have also been attempts in the prior art to optimise processes to obtain the protein in an optimal conformation to enable its subsequent reaction to the desired molecule. For example, WO 2007/003898 describes a specific diareduction step incorporated after purification of a Fab' to prepare it for subsequent reaction with PEG. In many cases, such as with a Fab', it is desirable to selectively affect one or more target cysteines for conjugation without reducing other cysteines present in the protein. For example in this case, Fab's have a native interchain disulphide bond between the heavy and light chain constant regions and so in order to selectively reduce a target cysteine elsewhere in the antibody, e.g. the hinge, reduction needs to be carried out with care so the disulphide chain remains intact and reaction with the interchain cysteines is avoided. Typically, this is achieved using what are considered to be mild reducing conditions. However, given that reduction is a common chemical reaction, even under said mild reducing conditions, different compounds present in a complex mixture are capable of reacting in a reducing environment resulting in altered properties, such as but not limited to binding behaviours, that can affect subsequent protein purification. For this reason reduction steps described in the prior art are performed once the protein has been purified. Subsequently, the desired protein conjugate must be purified from unreacted protein or other undesired conjugates. The efficiency of this coupling reaction process relates directly to production efficiency and associated manufacturing costs.

Given the above, there is a further need in the art to provide improved methods for protein manufacture, particularly where the manufactured protein is to be coupled to a second molecule.

DETAILED DESCRIPTION OF THE INVENTION

The present invention solves the above identified need by providing a novel method for manufacturing a protein, in particular where said protein is to be coupled with another molecule, particularly in industrial protein manufacturing to obtain proteins, e.g. for therapeutic purposes.

In a first embodiment, the invention provides a method for manufacturing a protein comprising:
  a) expressing the protein in a host cell,
  b) purifying said protein from a mixture containing the host cells and other contaminants wherein said purification comprises at least one chromatography step and wherein a reducing agent is added to said mixture and the protein is maintained in the presence of said reducing agent from the first chromatography step until the last chromatography step.

Typically, a first chromatography step serves as a protein capture step, for which there are different chromatography steps available to the skilled artisan, such as for example chromatography using beaded resins or membranes with appropriate functionality as solid phase for use in affinity chromatography, cation chromatography, anion chromatography, mixed mode chromatography, hydrophobic chromatography or hydrophobic charge induction chromatography. Product capture is usually performed in bind and elute mode, wherein binding of the protein of interest to the solid phase allows the impurities such as contaminating proteins to flow through the chromatographic medium while the protein of interest remains bound to the solid phase. The bound protein of interest is then recovered from the solid phase with an elution buffer that disrupts the mechanism by which the protein of interest is bound to said solid phase. The most appropriate product capture step will be determined based on the nature of the protein to be purified, for example a common product capture step when manufacturing a full length antibody is a Protein-A based affinity chromatography.

In a particular embodiment of the invention said first chromatography step is a cation exchange chromatography step, wherein the protein of interest binds to the chromatographic medium and is subsequently eluted into a first eluate containing the protein.

In a further particular embodiment of the method of the invention, a reducing agent is present in the buffers used during said cation exchange chromatography. More particularly, a reducing agent is present in the load buffer, in the wash buffer and in the elution buffer.

As discussed in the preceding section, a first chromatography step is generally followed by one or more subsequent chromatography steps to help remove further impurities, typically residual process and product related impurities. Generally such steps will employ a non-affinity chromatography step using a solid phase with appropriate functionality for use in gel filtration chromatography, cation chromatography, anion chromatography, mixed mode chromatography, hydrophobic chromatography and hydrophobic charge induction chromatography. These may be operated in bind and elute mode or in flow through mode. In flow-through mode, the impurities bind or have reduced mobility in the solid phase whereas the target protein is recovered in the eluate or flow through fraction.

In another particular embodiment of the invention, the first chromatography step is followed by an anion exchange chromatography step to capture impurities and produce a flow-through containing the protein.

In a further particular embodiment of the method of the invention, a reducing agent is present in the buffers used during said anion exchange chromatography to capture impurities and produce a flow-through containing the protein. More particularly, a reducing agent is present in the load buffer and in the elution buffer.

In a further particular embodiment of the method of the invention, the step of protein purification from a mixture comprises a first chromatography step that is a cation exchange chromatography from where a first eluate containing the protein is eluted, and a second chromatography step that is an anion exchange chromatography to produce a flow-through containing the protein.

In a further particular embodiment of the method of the invention, a reducing agent is present during said cation exchange chromatography and during said anion exchange chromatography. More particularly said reducing agent is present in the buffers used during said cation exchange chromatography and said anion exchange chromatography. In further embodiments one or more ultrafiltration or diafiltration (UF/DF) steps are performed between the chromatography steps. In industrial-scale protein manufacture, this is typically operated using a membrane based tangential flow filtration step performed for the purpose of product concentration and buffer exchange. These membranes are usually low protein binding and have a specific nominal molecular weight cutoff to prevent product loss, for example these include polyethersulfone (PES) membranes with a 10 kDa nominal molecular weight cutoff (T-series Omega PES membrane from Pall Life Sciences) or regenerated cellulose with a 10 kDa nominal molecular weight cutoff (Delta Regenerated Cellulose Membrane from Pall Life Sciences).

A purification strategy can include any of these steps in various combinations to suit the physical-chemical properties of the target protein. A particular purification strategy that can be used in accordance with the method of the present invention is that disclosed in WO 2012/013682, which is incorporated herein in its entirety.

In a further particular embodiment of the method of the invention, the step of protein purification from a mixture comprises a first chromatography step that is a cation exchange chromatography from where a first eluate containing the protein is eluted, a first ultrafiltration or diafiltration step applied to the first eluate, a second chromatography step that is an anion exchange chromatography to produce a flow-through containing the protein; and a second ultrafiltration or diafiltration step applied to the flow-through. More particularly, a reducing agent is present in all the buffers used during said cation exchange chromatography from where a first eluate containing the protein is eluted, during said first ultrafiltration or diafiltration step applied to the first eluate, and during said second chromatography step that is an anion exchange chromatography to produce a flow-through containing the protein.

In an alternative embodiment, the step of protein purification from a mixture comprises a first chromatography step from where a first eluate containing the protein is eluted, a first ultrafiltration or diafiltration step applied to the first eluate, a second chromatography step operated in bind and elute mode, from where a second eluate containing the protein is eluted. Preferably, a reducing agent is present in all buffers used during said first chromatography step from where a first eluate containing the protein is eluted, and during said first ultrafiltration or diafiltration step applied to the first eluate from where the protein is recovered in the presence of a reducing agent and applied to said second chromatography step, wherein the protein recovered in the eluate from said second chromatography step is essentially free of reducing agent.

There are a number of reducing agents available to the person skilled in the art. The most suitable reducing agent may be determined empirically for example by determining the reduced state of the target thiol in the recovered protein sample, for example using the free thiol assay as described in Lyons et al. 1990, Protein Engineering 3, 703. The most suitable reducing agent may also be chosen by means of determining the amount of undesirable intra- and inter-disulphide bond breakage in the recovered protein sample, or alternatively by measuring the amount of desired reacted protein molecules recovered for example by analytical size exclusion or reverse phase HPLC (high performance liquid chromatography). Size-exclusion HPLC separates particles on the basis of molecular size where large molecules flow through the column quicker than smaller ones. On the other hand, reverse-phase HPLC operates on the principle of hydrophobic interactions where binding of the molecule to the stationary phase is proportional to the contact surface area around the non-polar segment of the molecule upon association with the ligand on the stationary phase; retention times are longer for molecules that are less polar. In both cases the presence or absence of disulfide bonds results in species with different elution profiles.

In a second embodiment of the method of the invention, the reducing agent is selected from glutathione, β-mercaptoethanol, β-mercaptoethylamine, Tris(2-carboxyethyl)phosphine cysteine and combinations thereof.

In a third embodiment of the method of the invention, the reducing agent is 0.1 mM to 100 mM glutathione. The amount of reducing agent may be adjusted depending on the protein to be manufactured. In a further particular embodiment of the invention, said reducing agent is 0.1 mM to 20 mM, 0.1 mM to 10 mM, 0.5 mM to 5 mM, preferably 0.5 mM to 2 mM glutathione.

For the avoidance of doubt, the term glutathione as referred to herein refers to monomeric or reduced glutathione as defined by the CAS Number 70-18-8.

In a fourth embodiment of the method of the invention, the reducing agent is removed from the recovered protein.

There are different processes for removing reducing agents from a solution known to the skilled artisan, any of which may be suitable for the current process, including diafiltration, gel filtration, dialysis or a further chromatography step. In an alternative embodiment of the method of the invention the reducing agent is removed from the protein sample by diafiltration.

In a fifth embodiment of the method of the invention, the protein is coupled to another molecule.

Generally this process of coupling the protein to another molecule is performed in a solvent, for example an aqueous buffer solution such as phosphate, citrate or acetate. Typically this is the buffer into which the protein has been diafiltered or transferred by gel filtration. The reaction may generally be performed at any suitable temperature, for example between about 5° C. and about 70° C., for example at room temperature, i.e. at 20° C., 21° C. or 22° C. The buffer may optionally contain a chelating agent such as EDTA, EGTA, CDTA or DTPA. Alternatively or in addition the buffer may be a chelating buffer such as citric acid, oxalic acid, folic acid, bicine, tricine, or tris. The molecule will generally be employed in at least equimolar concentration relative to the concentration of the protein i.e. at least 1:1. Typically the molecule will be employed in excess concentration relative to the concentration of the protein. Typically the molecule is employed in between 1.1 and 100 fold molar excess, preferably 1.1, 1.5, 2, 3, 5, 10 or 50 fold molar excess. Further examples of suitable concentrations include a 1.2, 1.25, 1.3 and 1.4 fold molar excess. Alternatively where 2 or more proteins are coupled to a single molecule, said molecule may not be in excess, for example the ratio of molecule to protein may be between 0.1 and 1, preferably 0.5. The duration of the reaction may be determined empirically by a person skilled in the art and is typically between 1 and 20 hours. In one embodiment the reaction takes place over a period of 17 hours.

Where necessary, the desired protein coupled to other molecules may be separated from any starting materials or other products generated during the process by conventional means, for example by chromatography techniques such as ion exchange, size exclusion or hydrophobic interaction chromatography. Hence in one embodiment the method of the present invention further comprises an additional step in which the protein coupled to another molecule is recovered.

Said coupling may take place via one or more cysteines. The skilled artisan can establish empirically the number of cysteines in a protein available for coupling, for example, by determining the number of free thiols produced after the protein is treated with the reducing agent. Methods for determining the number of free thiols are well known in the art, see for example Lyons et al., 1990, Protein Engineering, 3, 703. Alternatively, the skilled artisan may analyze the resulting species resulting from the above reaction, for example by analytical reverse phase or size exclusion HPLC. Alternatively, the proteins may be modified by using various genetic engineering or protein engineering techniques to introduce cysteines into the protein for use as coupling sites. Hence the cysteines used for coupling may occur naturally in the protein and/or may be engineered into the protein by recombinant DNA techniques. Accordingly, the number and location of cysteines available for coupling can be specifically controlled depending on the intended use of the protein and the number of conjugated molecules required.

In a sixth embodiment of the method of the invention, the protein is coupled to another molecule via covalent binding to a cysteine residue on the protein.

In an alternative embodiment of the method of the invention, the protein is coupled to two or more molecules via cysteine residues.

In a seventh embodiment, the method of the invention further comprises a step of recovering the protein coupled to another molecule.

In an eighth embodiment of the method of the invention, the protein is an antibody or an antigen binding fragment thereof.

In a ninth embodiment of the method of the invention said antigen binding fragment is a Fab'.

In a further alternative embodiment, said Fab' specifically binds to TNF alpha. In a further more specific embodiment said Fab' that specifically binds to TNF alpha is CDP870 as disclosed in WO 01/094585 which is incorporated herein in its entirety.

In a tenth embodiment of the method of the invention said cysteine in said antibody or antigen binding fragment is in the antibody hinge.

As a skilled artisan is aware, it is possible to couple said antibody or antigen binding fragment to different molecules depending on the desired effect. As such said antibody or antigen binding fragment can be coupled for example to an antineoplastic agent, drug, toxin or biologically active peptide. On the other hand, said antibody or antigen binding fragment may be bound to an inert entity so as to increase its half-life in circulation, such as for example a naturally existing protein such as albumin or to a synthetic polymer such as polyethylene glycol (PEG).

In an eleventh embodiment of the method of the invention said molecule is a polyethylene glycol (PEG) molecule.

PEG molecules result from polymerization of ethylene oxide and are commercially available over a wide range of molecular weights from 300 Da to 10,000,000 Da. PEG molecules according to a particular embodiment of the present invention, may be linear or branched, purchased commercially or chemically synthesized according to known methods. While PEG molecules with different molecular weights find use in different applications, and have different physical properties such as viscosity due to chain length effects, their chemical properties don't vary significantly. The polymer size may in particular be selected on the basis of the intended use of the product for example ability to localize to certain tissues such as tumors or extend circulating half-life (for review see Chapman, 2002, Advanced Drug Delivery Reviews, 54, 531-545). Thus, for example, where the product is intended to leave the circulation and penetrate tissue, for example for use in the treatment of a tumor, it may be advantageous to use a small molecular weight polymer, for example with a molecular weight of around 5,000 Da. For applications where the product remains in the circulation, it may be advantageous to use a higher molecular weight polymer, for example having a molecular weight in the range from 25,000 Da to 40,000 Da.

PEG molecules are commercially available or can be synthesized, as a polyalkylene glycol compound or a derivative thereof, with or without coupling agents or derivatization with coupling or activating moieties (e.g., with thiol, triflate, tresylate, azirdine, oxirane, or preferably with a maleimide moiety, e.g., PEG-maleimide). Other appropriate polyalkylene glycol compounds include, but are not limited to, maleimido monomethoxy PEG, activated PEG polypropylene glycol, but also charged or neutral polymers of the following types: dextran, colominic acids, or other carbohydrate based polymers, polymers of amino acids, and biotin and other affinity reagent derivatives. Attaching PEG moieties is often referred to as PEGylation and refers to the process of reacting a protein with a PEG molecule wherein as a result of such reaction said PEG molecule is covalently bound to said protein.

As regards attaching PEG moieties in general, reference is made to "Poly(ethyleneglycol) Chemistry, Biotechnical and Biomedical Applications", 1992, J. Milton Harris (ed), Plenum Press, New York; "Poly(ethyleneglycol) Chemistry and Biological Applications", 1997, J. Milton Harris and S. Zalipsky (eds), American Chemical Society, Washington D.C. and "Bioconjugation Protein Coupling Techniques for the Biomedical Sciences", 1998, M. Aslam and A. Dent, Grove Publishers, New York.

When considering PEGylation and PEGylated proteins various aspects of the process have to be considered, such as the attachment site on the protein, activation type of the PEG reagent, nature (permanent or cleavable), length and shape of the linker, as well as length, shape and structure of the PEG reagent. PEGylation may be random where amino groups on the protein are targeted, and resulting in complex mixtures of various PEGylated species. Alternatively, PEGylation may be site-specific, typically via N-terminal and cysteine-specific reactions. Cysteine residues may be naturally present in native proteins. Alternatively, genetically introduced cysteines are used to direct the PEG molecule to an exactly determined site in the molecule. Accordingly, the number and location of cysteines available for PEgylation can be specifically controlled depending on the intended use of the protein and the number of PEG molecules required. A variety of thiol-specific reagents are available such as maleimide, pyridyl disulphide, vinyl sulfone, thiol reagents, etc. Due to the stability of the formed linkages, maleimide-PEG reagents are often a preferred choice.

In a further embodiment of the method of the invention, the PEG molecule is covalently bound via a maleimide group to a single cysteine on the protein.

In a particular embodiment, the PEG molecule is covalently bound via a maleimide group to a single cysteine present in the hinge region of an antibody or an antigen binding fragment thereof.

In a twelfth embodiment of the method of the invention, said PEG molecule is 40,000 PEG-maleimide.

In a particular embodiment said PEG molecule is branched 40,000 PEG-maleimide. More particularly said PEG molecule has 2 branches.

In a thirteenth embodiment, the method according to the eleventh or twelfth embodiments of the invention additionally comprises recovering the protein, wherein said protein is coupled to said PEG molecule via a cysteine.

In a particular embodiment of the method according to the twelfth embodiment of the invention, the protein coupled to said PEG molecule is recovered and further purified from uncoupled protein and PEG molecules by means known in the art such as for example a further chromatography step.

In a further particular embodiment, the protein coupled to said PEG molecule is an antibody or antigen-binding fragment thereof, more particularly said protein is a Fab'.

In a particular embodiment of the method of the invention, the antibody or antigen binding fragment thereof is bound to more than one PEG molecule. In another embodiment, the antibody or antigen binding fragment thereof is PEGylated on one or both heavy chains, or on one or both light chains, or on both heavy and light chains.

In a further particular embodiment of this invention, the antibody or antigen-binding region thereof that is coupled to a PEG molecule is a Fab' coupled to a PEG molecule on the heavy chain, the light chain or both. In a preferred embodiment, the protein is a Fab' coupled to a PEG molecule via a cysteine on the antibody hinge region. In certain embodiments, the PEGylated antibody has a hydrodynamic size of at least 24 kD. In other embodiments, the PEG may vary in size from anywhere from 20 to 60 kD (inclusive). In further embodiments, the PEG-linked antibody has a hydrodynamic size of at least 200 kD. In embodiments of the present invention where the antibody is linked to a PEG moiety, the PEGylated antibody may have an increased in vivo half-life relative to an antibody that lacks the PEG moiety.

In an alternative embodiment, the present invention refers to a method for manufacturing an antibody or antigen-binding fragment thereof coupled to a PEG molecule, comprising:
a) culturing a host cell under conditions such that they express the antibody or antigen-binding fragment thereof, and
b) purifying said antibody or antigen-binding fragment thereof from a mixture containing the host cells and other contaminants, wherein said purification comprises at least one chromatography step and wherein a reducing agent is added to said mixture and the antibody or antigen-binding fragment thereof is maintained in the presence of said reducing agent from the first chromatography step until the last chromatography step,
c) adding PEG to the antibody or antigen-binding fragment thereof, and
d) recovering said antibody or antigen-binding fragment thereof coupled to PEG.

Alternatively, the present invention refers to a method for purifying a protein, wherein said protein is expressed in a host cells under conditions such that they express the protein, comprising purifying said protein from a mixture containing the host cells and other contaminants, wherein said purification comprises at least one chromatography step and wherein a reducing agent is added to said mixture and the protein is maintained in the presence of said reducing agent from the first chromatography step until the last chromatography step.

An antibody or antibody fragment that can be manufactured in accordance with the method of the present invention can be produced by culturing eukaryotic host cells transfected with one or more expression vectors encoding the recombinant antibody fragment. The eukaryotic host cells are preferably mammalian cells, more preferably Chinese Hamster Ovary (CHO) cells. Mammalian cells may be cultured in any medium that will support their growth and expression of the recombinant protein, preferably the medium is a chemically defined medium that is free of animal-derived products such as animal serum and peptone. There are different cell culture mediums available to the person skilled in the art comprising different combinations of vitamins, amino acids, hormones, growth factors, ions, buffers, nucleosides, glucose or an equivalent energy source, present at appropriate concentrations to enable cell growth and protein production. Additional cell culture media components may be included in the cell culture medium at appropriate concentrations at different times during a cell culture cycle that would be known to those skilled in the art.

Mammalian cell culture can take place in any suitable container such as a shake flask or a bioreactor, which may or may not be operated in a fed-batch mode depending on the scale of production required. These bioreactors may be either stirred-tank or air-lift reactors. Various large scale bioreactors are available with a capacity of more than 1,000 L to 50,000 L, preferably between 5,000 L and 20,000 L, or to 10,000 L. Alternatively, bioreactors of a smaller scale such as between 2 L and 100 L may also be used to manufacture an antibody or antibody fragment according to the method of the invention.

An antibody or antigen-binding fragment thereof that can be manufactured in accordance with the methods of the present invention is typically found in the supernatant of a mammalian host cell culture, typically a CHO cell culture. For CHO culture processes wherein the protein of interest such as an antibody or antigen-binding fragment thereof is secreted in the supernatant, said supernatant is collected by methods known in the art, typically by centrifugation.

Therefore in a particular embodiment of the invention, the method comprises a step of centrifugation and supernatant recovery prior to protein purification. In a further particular embodiment said centrifugation is continuous centrifugation. For avoidance of doubt, supernatant denotes the liquid lying above the sedimented cells resulting from the centrifugation of the cell culture.

Alternatively, host cells are preferably prokaryotic cells, preferably gram-negative bacteria. More preferably, the host cells are *E. coli* cells. Prokaryotic host cells for protein expression are well known in the art (Terpe, K. (2006). Overview of bacterial expression systems for heterologous protein production: from molecular and biochemical fundamentals to commercial systems. Appl Microbiol Biotechnol 72, 211-222.). The host cells are recombinant cells which have been genetically engineered to produce the protein of interest such as an antibody fragment. The recombinant *E. coli* host cells may be derived from any suitable *E. coli* strain including from MC4100, TG1, TG2, DHB4, DH5α, DH1, BL21, K12, XL1 Blue and JM109. One example is *E. coli* strain W3110 (ATCC 27,325) a commonly used host strain for recombinant protein fermentations. Antibody fragments can also be produced by culturing modified *E. coli* strains, for example metabolic mutants or protease deficient *E. coli* strains.

An antibody fragment that can be purified in accordance with the methods of the present invention is typically found in either the periplasm of the *E. coli* host cell or in the host cell culture supernatant, depending on the nature of the protein, the scale of production and the *E. coli* strain used. The methods for targeting proteins to these compartments are well known in the art (Makrides, S. C. (1996). Strategies for achieving high-level expression of genes in *Escherichia coli*. Microbiol Rev 60, 512-538.). Examples of suitable signal sequences to direct proteins to the periplasm of *E. coli* include the *E. coli* PhoA, OmpA, OmpT, LamB and OmpF signal sequences. Proteins may be targeted to the supernatant by relying on the natural secretory pathways or by the induction of limited leakage of the outer membrane to cause protein secretion examples of which are the use of the pelB leader, the protein A leader, the co-expression of bacteriocin release protein, the mitomycin-induced bacteriocin release protein along with the addition of glycine to the culture medium and the co-expression of the kil gene for membrane permeabilization. Most preferably, in the methods of the invention, the recombinant protein is expressed in the periplasm of the host *E. coli*.

Expression of the recombinant protein in the *E. coli* host cells may also be under the control of an inducible system, whereby the expression of the recombinant antibody in *E. coli* is under the control of an inducible promoter. Many inducible promoters suitable for use in *E. coli* are well known in the art and depending on the promoter expression of the recombinant protein can be induced by varying factors such as temperature or the concentration of a particular substance in the growth medium. Examples of inducible promoters include the *E. coli* lac, tac, and trc promoters which are inducible with lactose or the non-hydrolyzable lactose analog, isopropyl-b-D-1-thiogalactopyranoside (IPTG) and the phoA, trp and araBAD promoters which are induced by phosphate, tryptophan and L-arabinose respectively. Expression may be induced by, for example, the addition of an inducer or a change in temperature where induction is temperature dependent. Where induction of recombinant protein expression is achieved by the addition of an inducer to the culture the inducer may be added by any suitable method depending on the fermentation system and the inducer, for example, by single or multiple shot additions or by a gradual addition of inducer through a feed. It will be appreciated that there may be a delay between the addition of the inducer and the actual induction of protein expression for example where the inducer is lactose there may be a delay before induction of protein expression occurs while any pre-existing carbon source is utilized before lactose. *E. coli* host cell cultures (fermentations) may be cultured in any medium that will support the growth of *E. coli* and expression of the recombinant protein. The medium may be any chemically defined medium such as e.g. described in Durany O,C.G.d.M.C.L.-S.J. (2004). Studies on the expression of recombinant fuculose-1-phosphate aldolase in *Escherichia coli*. Process Biochem 39, 1677-1684.

Culturing of the *E. coli* host cells can take place in any suitable container such as a shake flask or a fermenter depending on the scale of production required. Various large scale fermenters are available with a capacity of more than 1,000 liters up to about 100,000 liters. Preferably, fermenters of 1,000 to 50,000 liters are used, more preferably 1,000 to 25,000, 20,000, 15,000, 12,000 or 10,000 liters. Smaller scale fermenters may also be used with a capacity of between 0.5 and 1,000 liters.

Fermentation of *E. coli* may be performed in any suitable system, for example continuous, batch or fed-batch mode depending on the protein and the yields required. Batch mode may be used with shot additions of nutrients or inducers where required. Alternatively, a fed-batch culture may be used and the cultures grown in batch mode pre-induction at the maximum specific growth rate that can be sustained using the nutrients initially present in the fermenter and one or more nutrient feed regimes used to control the growth rate until fermentation is complete. Fed-batch mode may also be used pre-induction to control the metabolism of the *E. coli* host cells and to allow higher cell densities to be reached.

If desired, the host cells may be subject to collection from the fermentation medium, e.g. host cells may be collected from the sample by centrifugation, filtration or by concentration.

In one embodiment the process according to the present invention comprises a step of centrifugation and cell recovery prior to extracting the protein.

For *E. coli* fermentation processes wherein the protein of interest such as an antibody fragment is found in the periplasmic space of the host cell it is required to release the protein from the host cell. The release may be achieved by any suitable method such as cell lysis by mechanical or pressure treatment, freeze-thaw treatment, osmotic shock, extraction agents or heat treatment. Such extraction methods for protein release are well known in the art. Therefore in a particular embodiment, the method of the invention comprises an additional protein extraction step prior to protein purification. In a more particular embodiment, said protein extraction step is performed in the presence of a reducing agent.

In a further embodiment of the method according to the invention, further comprises recovering the host cells from the cell culture medium, harvesting the protein using a protein extraction step performed in the presence of a reducing agent, recovering the protein containing mixture resulting from the protein extraction step and purifying said protein from the mixture wherein said purification comprises at least one chromatography step and wherein a reducing agent is added to said mixture and the protein is maintained in the presence of said reducing agent from the first chromatography step until the last chromatography step.

In a further embodiment of the method according to the invention, the reducing agent present during said protein extraction step according to the above embodiment may be the same or different from the reducing agent present during protein purification step of the method of the invention.

In a preferred embodiment an extraction buffer is added to the sample and the sample is then subjected to a heat treatment step. The heat treatment step is preferably as described in detail in U.S. Pat. No. 8,969,036. The heat treatment step makes it possible to obtain a sample of soluble, correctly folded and assembled antibody fragment by facilitating the removal of other antibody-related material.

The heat treatment step is performed by subjecting the sample to a desired elevated temperature. Most preferably, the heat treatment step is performed within the range of 30° C. to 70° C. The temperature can be selected as desired and may depend on the stability of the antibody for purification. In another embodiment, the temperature is within the range 40° C. to 65° C., or preferably within the range 40° C. to 60° C., more preferably within the range 45° C. to 60° C., even more preferably within the range 50° C. to 60° C. and most preferably at 55° C. to 60° C., 58° C. to 60° C. or 59° C. Thus, the minimum temperatures are 30° C., 35° C. or 40° C. and the maximum temperatures 60° C., 65° C. or 70° C.

The heat treatment step is preferably carried out for a prolonged period of time. The length of heat treatment is preferably between 1 and 24 hours, more preferably between 4 and 18 hours, even more preferably between 6 and 16 hours and most preferably between 10 and 14 hours or between 10 and 12 hours, for example 12 hours. Thus, the minimum time for heat treatment is 1, 2 or 3 hours and the maximum is 20, 22 or 24 hours.

In a particular embodiment, the heat treatment is performed at 50° C. to 60° C. for 10 to 16 hours, and more preferably at 59° C. for 10 to 12 hours. One skilled in the art will understand that temperatures and time can be selected as suits the sample in question and the characteristics of the antibody being produced.

Following the step of extraction the mixture containing the protein of interest such an antibody fragment may be subjected to a step of centrifugation and/or filtration.

In a further particular embodiment, the method of the invention may comprise a step of adjusting the pH of the mixture containing the protein of interest following the extraction step and prior to purification of the protein from said mixture.

In a further embodiment of the method of protein manufacture according to the invention, a reducing agent is also present during said heat treatment step. In a particular embodiment, the extraction buffer that is added to the sample contains said reducing agent. In this sense the reducing agent present during said heat treatment step may be the same or different to the reducing agent present during protein purification according to the method of the invention.

In a further particular embodiment of the method of the invention the reducing agent present during the heat treatment step is selected from glutathione, β-mercaptoethanol, β-mercaptoethylamine, Tris(2-carboxyethyl)phosphine cysteine and combinations thereof.

In a further particular embodiment of the method of the invention, the reducing agent present during the heat treatment step is 0.1 mM to 100 mM glutathione. The amount of reducing agent may be adjusted depending on the protein to be manufactured. In a further particular embodiment of the invention, said glutathione is present in an amount 0.5 mM to 80 mM, 1 mM to 50 mM, 1 mM to 25 mM, preferably 1 mM to 10 mM.

Definitions

The term "antibody" or "antibodies" as used herein refers to monoclonal or polyclonal antibodies. The term "antibody" or "antibodies" as used herein includes but is not limited to recombinant antibodies that are generated by recombinant technologies as known in the art. "Antibody" or "antibodies" include antibodies' of any species, in particular of mammalian species; such as human antibodies of any isotype, including $IgA_1$, $IgA_2$, IgD, $IgG_1$, $IgG_{2a}$, $IgG_{2b}$, $IgG_3$, $IgG_4$, IgE and IgM and modified variants thereof, non-human primate antibodies, e.g. from chimpanzee, baboon, rhesus or cynomolgus monkey; rodent antibodies, e.g. from mouse, rat or rabbit; goat or horse antibodies; and camelid antibodies (e.g. from camels or llamas such as Nanobodies™) and derivatives thereof; or of bird species such as chicken antibodies or of fish species such as shark antibodies. The term "antibody" or "antibodies" also refers to "chimeric" antibodies in which a first portion of at least one heavy and/or light chain antibody sequence is from a first species and a second portion of the heavy and/or light chain antibody sequence is from a second species. Chimeric antibodies of interest herein include "primatized" antibodies comprising variable domain antigen-binding sequences derived from a non-human primate (e.g. Old World Monkey, such as baboon, rhesus or cynomolgus monkey) and human constant region sequences. "Humanized" antibodies are chimeric antibodies that contain a sequence derived from non-human antibodies. For the most part, humanized antibodies are human antibodies (recipient antibody) in which residues from a hypervariable region of the recipient are replaced by residues from a hypervariable region [or complementarity determining region (CDR)] of a non-human species (donor antibody) such as mouse, rat, rabbit, chicken or non-human primate, having the desired specificity, affinity, and activity. In most instances residues of the human (recipient) antibody outside of the CDR; i.e. in the framework region (FR), are additionally replaced by corresponding non-human residues. Furthermore, humanized antibodies may comprise residues that are not found in the recipient antibody or in the donor antibody. These modifications are made to further refine antibody performance. Humanization reduces the immunogenicity of non-human antibodies in humans, thus facilitating the application of antibodies to the treatment of human disease. Humanized antibodies and several different technologies to generate them are well known in the art. The term "antibody" or "antibodies" also refers to human antibodies, which can be generated as an alternative to humanization. For example, it is possible to produce transgenic animals (e.g., mice) that are capable, upon immunization, of producing a full repertoire of human antibodies in the absence of production of endogenous murine antibodies. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies with specificity against a particular antigen upon immunization of the transgenic animal carrying the human germ-line immunoglobulin genes with said antigen. Technologies for producing such transgenic animals and technologies for isolating and producing the human antibodies from such transgenic animals are known in the art. Alternatively, in the transgenic animal; e.g. mouse, only the immunoglobulin genes coding for the variable regions of the mouse antibody are replaced with corresponding human variable immunoglobulin gene sequences. The mouse germline immunoglobulin genes coding for the antibody constant regions remain unchanged. In this way, the antibody effector functions in the immune system of the transgenic mouse and consequently the B cell development is essentially unchanged, which may lead to an improved antibody response upon antigenic challenge in vivo. Once the genes coding for a particular antibody of interest have been isolated from such transgenic animals the genes coding for the constant regions can be replaced with human constant region genes in order to obtain a fully human antibody. Other methods for obtaining human antibodies/antibody fragments in vitro are based on display technologies such as phage display or ribosome display technology, wherein recombinant DNA libraries are used that are either generated at least in part artificially or from immunoglobulin variable (V) domain gene repertoires of donors. Phage and ribosome display technologies for generating human antibodies are well known in the art. Human antibodies may also be generated from isolated human B cells that are ex vivo immunized with an antigen of interest and subsequently fused to generate hybridomas which can then be screened for the optimal human antibody. The term "antibody" or "antibodies" as used herein, also refers to an aglycosylated antibody.

The term "antibody fragment" as used herein refers to antibody molecule which comprises at least one heavy or light chain immunoglobulin domain as known in the art and binds to an antigen. Examples of antibody fragments according to the invention include Fab, Fab', F(ab')$_2$, and Fv and scFv fragments; as well as diabodies; triabodies; tetrabodies; minibodies; domain antibodies; (dAbs), such as sdAbs, $V_HH$ and $V_{NAR}$ fragments, single-chain antibodies; bispecific, trispecific, tetraspecific or multispecific antibodies formed from antibody fragments or antibodies, including but not limited to Fab-Fv or Fab-Fv-Fv constructs. Antibody fragments as defined above are known in the art.

The term "chromatography" as used herein refers to the process by which a solute of interest in a mixture is separated from the other solutes in a mixture as a result of differences in rates at which the individual solutes of the mixture migrate through a stationary medium under the influence of a moving phase.

The term "anion exchange chromatography" as used herein refers to a chromatography wherein the solid phase is positively charged, e.g. having one or more positively charged ligands, such as quaternary amino groups, attached thereto. Commercially available anion exchange resins include DEAE cellulose, QAE SEPHADEX™ and FAST Q SEPHAROSE™ (GE Healthcare).

The term "cation exchange chromatography" as used herein refers to a chromatography wherein the solid phase which is negatively charged, e.g. having one or more negatively charged ligands, such as for example a carboxylate or sulphonate group. Commercially available cation exchange resins include carboxy-methyl-cellulose, sulphopropyl (SP) immobilized on agarose and sulphonyl immobilized on agarose.

The term "wash buffer" as used herein refers to a buffer used to wash or re-equilibrate the ion exchange resin, prior to eluting the polypeptide molecule of interest. Conveniently, the wash buffer and loading buffer may be the same, but this is not required.

The term "load buffer" as used herein refers to the buffer used to load the protein of interest onto the solid phase.

The term "elution buffer" as used herein refers to the buffer used to elute the protein of interest from the solid phase. This may be achieved by using additives, and/or conductivity and/or pH ranges of the elution buffer such that the polypeptide of interest is eluted from the solid phase of the chromatography.

The term "ultrafiltration" as used herein refers to a pressure-driven process wherein a mixture such as a solution, e.g. containing a protein of interest, is passed through a membrane for concentration or purification purposes. Ultrafiltration membranes typically have a mean pore size between 1 and 50 nm, which is between the mean pore size of reverse osmosis and microfiltration membranes. The pore size is usually quantified by its ability to retain proteins of certain molecular weights and is normally quoted in terms of a nominal molecular weight cut off (NMWCO) in kDa. Ultrafiltration separates solutes based on differences in the rate of filtration of different substances across the membrane in response to a given pressure driving force which rate is dependent on the size of the solute. Thus, the solutes in the mixture or solution are separated on the bases of size differences. Ultrafiltration is frequently used in downstream processing for protein concentration, buffer exchange and desalting, protein purification, virus clearance, and clarification. The term "ultrafiltration" includes tangential flow filtration (TFF) whereby the mixture such as solution is passed horizontally along the ultrafiltration membrane. The term "ultrafiltration" does not include high performance tangential flow filtration (HPTFF) whereby the solutes are separated not just on the basis of size, but size and charge.

The term "diafiltration" as used herein refers to a type of ultrafiltration membrane technique for essentially replacing the concentration of salts or solvents from solutions containing proteins, peptides, nucleic acids, and other biomolecules. The process selectively uses permeable membrane filters to separate the components of solutions and suspensions based on their molecular size. Smaller molecules such as salts, solvents, and water pass freely through the ultrafiltration membrane, which retains the larger molecules. A protein sample, typically in a buffer, is diafiltered across a membrane which retains the protein and allows buffer exchange. Over time the original buffer containing the protein is replaced with a new buffer.

Alternatively, depending on the experimental scale, it may be of interest to use gel filtration (such as Sephadex G-25 desalting columns operated under gravity flow) as a means to replace the original buffer with a new buffer. In this case buffer replacement occurs when molecules larger than the resin pores are excluded from said resin pores and travel faster through the solid phase than smaller molecules that diffuse into the resin pores and are therefore retained and move more slowly through the phase. The larger molecules such as the desired protein are collected in fractions eluted in the resin equilibration buffer.

The term "PEGylated" as used herein refers to a protein that has been covalently bound to a PEG molecule.

EXAMPLES

Example 1

Fab'1 (a Fab' antibody fragment containing a single hinge thiol intended for site specific PEGylation) was expressed as a heterologous protein in $E.\ coli$ W3110 host cells and the heterologous protein was released from the periplasmic space of the host cells by the addition of 100 mM Tris/10 mM-EDTA buffer adjusted to pH 7.4 and heat treatment at 57.5° C. Cellular material was removed through centrifugation and the cell extract containing the heterologous protein was adjusted through addition of acetic acid to a pH 4.5. The pH adjusted cell extract was then clarified using a combination of centrifugation and 0.2 μm filtration. The clarified extract (feed stream) was then diluted with a water to target a conductivity of approximately 6.0 mS/cm.

The feed stream containing the Fab'1 was then loaded onto a Capto S™ cation exchange column from GE Healthcare [highly cross-linked rigid agarose bead (mean particle size 90 μm) with a sulphonate cation exchange ligand attached via a dextran linker (ionic capacity 0.11-0.14 mmol Na+/ml)]. The column had been equilibrated prior to feed stream loading with 6 column volumes of 50 mM sodium acetate buffer adjusted to pH 4.5 with acetic acid.

After loading the column was washed with 50 mM sodium acetate buffer adjusted to pH 4.5 with acetic acid, until all the unbound material was washed off. The Fab'1-containing fraction was eluted with 50 mM sodium acetate and 190 mM NaCl adjusted to pH 4.5 with acetic acid.

The resulting Fab'1 containing eluate was subjected to ultrafiltration using a polyether sulphone-based ultrafiltration membrane with a nominal molecular weight cut-off of 10 kDa (T-series membrane (Pall Corporation)) resulting in a concentration to approximately a fifth of the volume and diafiltered against approximately 8 volumes of 20 mM Tris buffer adjusted to pH 8.2.

The Fab'1 pool was loaded onto a Capto Q™ anion exchange chromatography column from GE Healthcare [highly cross-linked rigid agarose bead (mean particle size 90 μm) with a quaternary amine anion exchange ligand attached via a dextran linker (ionic capacity 0.16-0.22 mmol Cl-/ml)]. The column had been equilibrated prior to protein load with 20 mM Tris buffer adjusted to pH 8.2.

After loading the column, the column was washed using 20 mM Tris buffer adjusted to pH 8.2 Fab'1 was recovered in the flow-through fraction resulting from loading and washing steps.

The resulting anion exchange chromatography eluate containing Fab'1 was loaded onto a PD-10 desalting column from GE Healthcare (gel filtration chromatography with a Sephadex™ G25 matrix having a particle size range of 85 to 260 um and an exclusion limit of 5000 Da), using 20 mM sodium acetate buffer adjusted to pH 4.5 as pre-equilibration, post load wash and elution buffer.

The Fab'1 eluate was recovered and 40 kDa PEG-maleimide having 2 branches of 20 kDa (3-Bis(methylpolyoxyethylene-oxy)-1-([3-(6-maleimido-1-oxohexyl)amino] propyloxy) propane, NOF Corporation, Tokyo, Japan) was added at a Fab'1-PEG molar ratio of 1:2 and allowed to react for 17 hours at 18-22° C.

Figure 1:
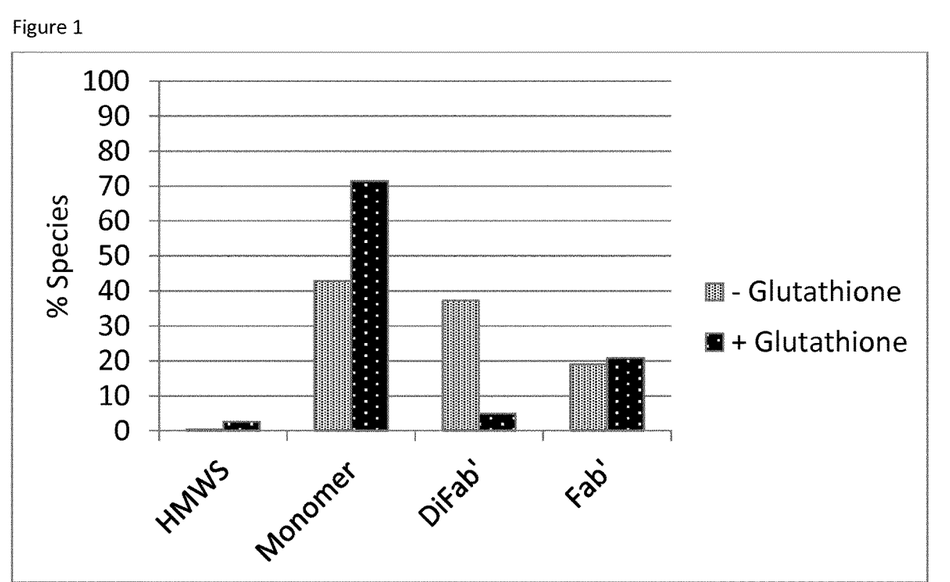
FIG. 1 shows size exclusion HPLC analysis of the samples obtained from the PEGylation reaction of Fab'1 recovered from two parallel purification processes performed from an *E. coli* periplasmic extract obtained from cells expressing Fab'1. One process is performed under control conditions, i.e. without glutathione, whereas in the second process the protein was maintained in the presence of 1 mM glutathione from the first chromatography step to capture the protein to the final chromatography step. HMWS refers to the amount of high molecular weight species or aggregates, monomer refers to the amount of Fab'1 coupled to PEG, diFab' refers to the amount of Fab'1 dimers, and Fab' refers to the amount of remaining unbound Fab'1.

PEGylation efficiency as determined using size exclusion HPLC resulted in the generation of 43% Fab'1-PEG monomer (FIG. 1).

Example 2

CDP870 Fab' was expressed as a heterologous protein in E. coli W3110 host cells and the heterologous protein was released from the periplasmic space of the host cells by the addition of 100 mM Tris/10 mM-EDTA buffer adjusted to pH 7.4 and heat treatment at 59° C. Cellular material was removed through centrifugation and the cell extract containing the heterologous protein was adjusted through addition of acetic acid to a pH 4.5. The pH adjusted cell extract was then clarified using a combination of centrifugation and 0.2 µm filtration.

The clarified extract (feed stream) was then diluted with water to a target conductivity of approximately 4 mS/cm and supplemented with 1 mM glutathione The feed stream containing the CDP870 Fab' was then loaded onto a Capto S™ cation exchange column from GE Healthcare [highly cross-linked rigid agarose bead (mean particle size 90 µm) with a sulphonate cation exchange ligand attached via a dextran linker (ionic capacity 0.11-0.14 mmol Na+/ml)]. The column had been equilibrated prior to feed stream loading with 6 column volumes of 50 mM sodium acetate buffer (adjusted to pH 4.5 with acetic acid) containing 1 mM glutathione.

After loading the column was washed with 50 mM sodium acetate buffer adjusted to pH 4.5 with acetic acid containing 1 mM glutathione, until the all the unbound material was washed off. The CDP870 Fab' fraction was eluted with 50 mM sodium acetate and 250 mM NaCl (adjusted to pH 4.5 with acetic acid) containing 1 mM glutathione.

The resulting CDP870 Fab' containing eluate was subjected to ultrafiltration using a polyether sulphone-based ultrafiltration membrane with a nominal molecular weight cut-off of 10 kDa (T-series membrane (Pall Corporation)) resulting in a concentration to approximately a half of the volume and diafiltered into 20 mM Tris buffer adjusted to pH 8.5 buffer containing 1 mM glutathione. 7 volumes of buffer were carried out for the diafiltration.

The pool was loaded onto a Capto Q™ anion exchange chromatography column from GE Healthcare [highly cross-linked rigid agarose bead (mean particle size 90 µm) with a quaternary amine anion exchange ligand attached via a dextran linker (ionic capacity 0.16-0.22 mmol Cl–/ml)]. The column had been equilibrated prior to protein load with 20 mM Tris buffer adjusted to pH 8.5 containing 1 mM glutathione.

After loading, the column was washed using 20 mM Tris buffer adjusted to pH 8.5 containing 1 mM glutathione. CDP870 Fab' was recovered in the flow-through fraction resulting from the loading and washing steps. The resulting anion exchange chromatography eluate containing CDP870 Fab' was loaded onto a PD-10 desalting column from GE Healthcare (gel filtration chromatography with a Sephadex™ G25 matrix having a particle size range of 85 to 260 um and an exclusion limit of 5000 Da), using 20 mM sodium acetate buffer adjusted to pH 4.5 with acetic acid as pre-equilibration, post load wash and elution buffer.

The CDP870 Fab' containing eluate was recovered and 40 kDa PEG having 2 branches of 20 kDa (Maleimidopropionamide of bis (Methoxypoly(ethylene glycol)), modified lysine, Nektar Therapeutics Corporation, California, US) containing a maleimide linker was added at a PEG molar ratio excess of 1:2.8, and allowed to react at 18-22° C.

Figure 2:
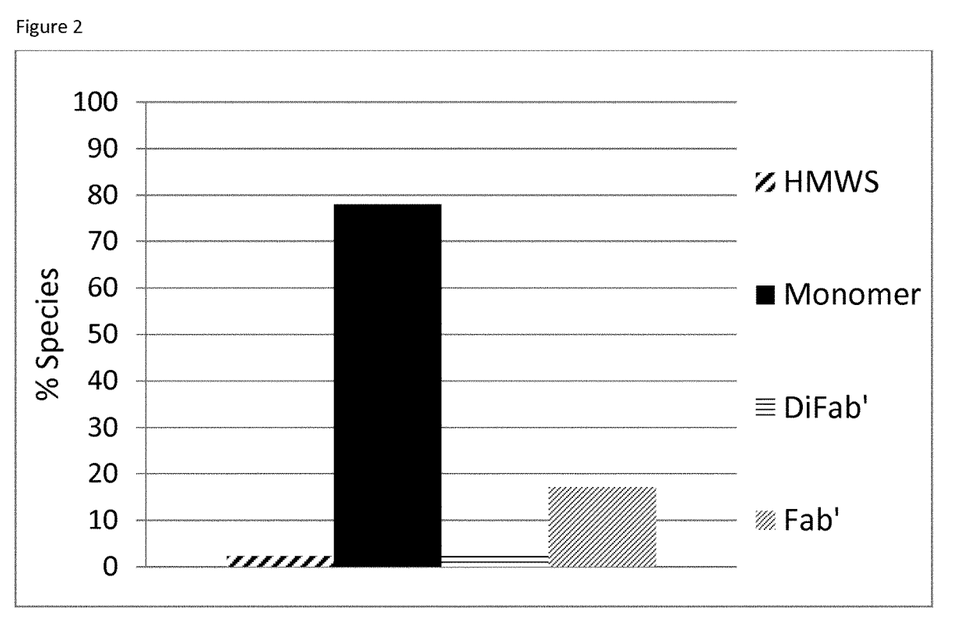
FIG. 2 shows size exclusion HPLC analysis of the samples obtained from the PEGylation reaction of CDP870 Fab' recovered from an E. coli periplasmic extract obtained from cells expressing CDP870 Fab', and subsequently purified while maintaining the protein in the presence of 1 mM glutathione from the first chromatography step to capture the protein to the final chromatography step. HMWS refers to the amount of high molecular weight species or aggregates, monomer refers to the amount of CDP870 Fab' coupled to PEG, diFab' refers to the amount of CDP870 Fab'Fab'2 dimers, and Fab' refers to the amount of remaining uncoupled.

PEGylation efficiency as determined using size exclusion HPLC resulted in the generation of 78.1% CDP870 Fab'-PEG monomer (FIG. 2).

Example 3

CDP870 Fab' was expressed as a heterologous protein in E. coli W3110 host cells and the heterologous protein was released from the periplasmic space of the host cells by the addition of 100 mM Tris/10 mM-EDTA buffer adjusted to pH 7.4 and containing 1 mM glutathione and heat treatment at 59° C. Cellular material was removed through centrifugation and the cell extract containing the heterologous protein was adjusted through addition of acetic acid to a pH 4.5. The pH adjusted cell extract was then clarified, by 0.2 µm filtration.

The clarified extract (feed stream) was then diluted with water to a target conductivity of 4 mS/cm and supplemented with 1 mM glutathione The feed stream containing the CDP870 Fab' was then loaded onto a Capto S™ cation exchange column from GE Healthcare [highly cross-linked rigid agarose bead (mean particle size 90 µm) with a sulphonate cation exchange ligand attached via a dextran linker (ionic capacity 0.11-0.14 mmol Na+/ml)]. The column had been equilibrated prior to feed stream loading with 6 column volumes of 50 mM sodium acetate buffer containing 1 mM glutathione adjusted to pH 4.5 with acetic acid.

After loading the column was washed with 50 mM sodium acetate buffer adjusted to pH 4.5 with acetic acid containing 1 mM glutathione, until the all the unbound material was washed off. The CDP870 Fab' fraction was eluted with 50 mM sodium acetate and 250 mM NaCl containing 1 mM glutathione adjusted to pH 4.5 with acetic acid The resulting CDP870 Fab' containing eluate was subjected to ultrafiltration using a polyether sulphone-based ultrafiltration membrane with a nominal molecular weight cut-off of 10 kDa resulting in a concentration to approximately a third of the volume and diafiltered against 9 volumes of 20 mM Tris buffer adjusted to pH 8.5 buffer containing 1 mM glutathione. The CDP870 Fab' pool was loaded onto a Capto Q™ anion exchange chromatography column from GE Healthcare [highly cross-linked rigid agarose bead (mean particle size 90 µm) with a quaternary amine anion exchange ligand attached via a dextran linker (ionic capacity 0.16-0.22 mmol Cl–/ml)]. The column had been equilibrated prior to protein load with 20 mM Tris buffer adjusted to pH 8.5 containing 1 mM glutathione. After loading, the column was washed using 20 mM Tris buffer adjusted to pH 8.5 containing 1 mM glutathione CDP870 Fab' was recovered in the flow-through fraction resulting from the loading and washing steps.

The resulting CDP870 Fab' containing eluate was subjected to ultrafiltration using a polyether sulphone-based ultrafiltration membrane with a nominal molecular weight cut-off of 10 kDa and diafiltered into 20 mM sodium acetate pH 4.5 in preparation for PEGylation.

40 kDa PEG-maleimide having 2 branches of 20 kDa (Maleimidopropionamide of bis (Methoxypoly(ethylene glycol)), modified lysine, Nektar Therapeutics Corporation, California, US) was added to the recovered protein at CDP870 Fab':PEG molar ratios of 1:1.4 and 1:2 and allowed to react for 17 hours at 18-22° C.

PEGylation efficiency as determined by Reverse Phase HPLC chromatography revealed the generation of 74% and 74.4% CDP870 Fab'-PEG monomer for the 1:1.4 and 1:2 CDP870 Fab':PEG ratio, respectively.

Example 4

Fab'1 (a Fab' antibody fragment containing a single hinge thiol intended for site specific PEGylation) was expressed as a heterologous protein in *E. coli* W3110 host cells and the heterologous protein was released from the periplasmic space of the host cells by the addition of 100 mM Tris/10 mM-EDTA buffer adjusted to pH 7.4 containing 10 mM glutathione and heat treatment at 57.5° C. Cellular material was removed through centrifugation and the cell extract containing the heterologous protein was adjusted through addition of acetic acid to pH 4.5. The pH adjusted cell extract was then clarified using a combination of centrifugation and 0.2 µm filtration.

The clarified extract (feed stream) was then diluted with water to a 6 mS/cm conductivity range (a dilution factor of approximately 4) The feed stream containing the Fab'1 was then loaded onto a Capto S™ cation exchange column from GE Healthcare [highly cross-linked rigid agarose bead (mean particle size 90 µm) with a sulphonate cation exchange ligand attached via a dextran linker (ionic capacity 0.11-0.14 mmol Na+/ml)]. The column had been equilibrated prior to feed stream loading with 6 column volumes of 50 mM sodium acetate buffer containing 1 mM glutathione adjusted to pH 4.5 with acetic acid.

After loading the column was washed with 50 mM sodium acetate buffer containing 1 mM glutathione adjusted to pH 4.5 with acetic acid, until all the unbound material was washed off. The Fab'1-containing fraction was eluted with a 50 with 50 mM sodium acetate and 190 mM NaCl containing 1 mM glutathione adjusted to pH 4.5 with acetic acid.

The resulting Fab'1 containing eluate was subjected to ultrafiltration using a polyether sulphone-based ultrafiltration membrane with a nominal molecular weight cut-off of 10 kDa resulting in a concentration to approximately a fifth of the volume and diafiltered against 8 volumes of 20 mM Tris buffer containing 1 mM glutathione adjusted to pH 8.2 buffer.

The Fab'1 pool was loaded onto a Capto Q™ anion exchange chromatography column from GE Healthcare [highly cross-linked rigid agarose bead (mean particle size 90 µm) with a quaternary amine anion exchange ligand attached via a dextran linker (ionic capacity 0.16-0.22 mmol Cl−/ml)]. The column had been equilibrated prior to protein load with 20 mM Tris buffer containing 1 mM glutathione adjusted to pH 8.2.

After loading the column, the column was washed using 20 mM Tris buffer containing 1 mM glutathione adjusted to pH 8.2. Fab'1 was recovered in the flow-through fraction resulting from the loading and washing steps.

The resulting anion exchange chromatography eluate containing Fab'1 was loaded onto a PD-10 desalting column from GE Healthcare (gel filtration chromatography with a Sephadex™ G25 matrix having a particle size range of 85 to 260 um and an exclusion limit of 5000 Da), using 20 mM sodium acetate buffer adjusted to pH 4.5 as pre-equilibration, post load wash and elution buffer.

The Fab'1 eluate was recovered and 40 kDa PEG-maleimide having 2 branches of 20 kDa (3-Bis(methylpolyoxyethylene-oxy)-1-([3-(6-maleimido-1-oxohexyl)amino] propyloxy) propane, NOF Corporation, Tokyo, Japan) was added at a Fab'1-PEG molar ratio of 1:2 and allowed to react for 17 hours at 20° C.

PEGylation efficiency as determined using size exclusion HPLC resulted in the generation of 71.5% Fab'1-PEG monomer (FIG. 1).

Example 5

Fab'1 (a Fab' antibody containing a single hinge thiol intended for site specific PEGylation) was expressed as a heterologous protein in *E. coli* W3110 host cells and the heterologous protein was released from the periplasmic space of the host cells by the addition of 100 mM Tris/10 mM-EDTA buffer adjusted to pH 7.4 and heat treatment at 57.5° C. Cellular material was removed through centrifugation and the cell extract containing the heterologous protein was adjusted through addition of acetic acid to a pH 4.5. The pH adjusted cell extract was then clarified using a combination of centrifugation and 0.2 µm filtration.

The clarified extract (feed stream) was then diluted with water to a conductivity of 6 mS/cm. The feed stream containing the Fab'1 was then loaded onto a Capto S™ cation exchange column from GE Healthcare [highly cross-linked rigid agarose bead (mean particle size 90 µm) with a sulphonate cation exchange ligand attached via a dextran linker (ionic capacity 0.11-0.14 mmol Na+/ml)]. The column had been equilibrated prior to feed stream loading with 50 mM sodium acetate buffer adjusted to pH 4.5 with acetic acid.

After loading the column was washed with 50 mM sodium acetate buffer adjusted to pH 4.5 with acetic acid, until all the unbound material was washed off. The Fab'1-containing fraction was eluted with 50 mM sodium acetate and 190 mM NaCl adjusted to pH 4.5 with acetic acid.

The resulting Fab'1 containing eluate was subjected to ultrafiltration in using a polyether sulphone-based ultrafiltration membrane with a nominal molecular weight cut-off of 10 kDa resulting in a concentration approximately a fifth of the volume and diafiltered with 8 volumes of 20 mM Tris buffer adjusted to pH 8.2. The Fab'1 pool was loaded onto a Capto Q™ anion exchange chromatography column from GE Healthcare [highly cross-linked rigid agarose bead (mean particle size 90 µm) with a quaternary amine anion exchange ligand attached via a dextran linker (ionic capacity 0.16-0.22 mmol Cl−/ml)]. The column had been equilibrated prior to protein load with 20 mM Tris buffer adjusted to pH 8.2.

After loading the column, the column was washed using 20 mM Tris buffer adjusted to pH 8.2. Fab'1 was recovered in the flow-through fraction resulting from the loading and washing steps.

Recovered anion exchange chromatography eluate containing Fab'1 was then subjected to ultrafiltration using a polyether sulphone-based ultrafiltration membrane with a nominal molecular weight cut-off of 10 kDa to concentrate it to 20 mg/ml and diafiltered into a 0.1 M phosphate buffer pH 6.8 containing 2 mM EDTA.

The resulting Fab'1 containing sample was then reduced by diafiltration using the same membrane and 0.1 M phosphate buffer containing 2 mM EDTA and 1 mM 2-mercaptoethylamine adjusted to pH 6.8 over 6.5 hours.

A further ultrafiltration/diafiltration into 20 mM sodium acetate buffer pH adjusted to 4.5 was performed on the same membrane to remove the reducing agent in preparation for PEGylation.

40 kDa PEG-maleimide having 2 branches of 20 kDa (3-Bis(methylpolyoxyethylene-oxy)-1-([3-(6-maleimido-1-oxohexyl)amino]propyloxy) propane, NOF Corporation, Tokyo, Japan) was added to the recovered Fab'1 protein at a Fab':PEG weight to weight ratio of 1:1.25 and allowed to react during 17 hours at 18-22° C.

Figure 3:
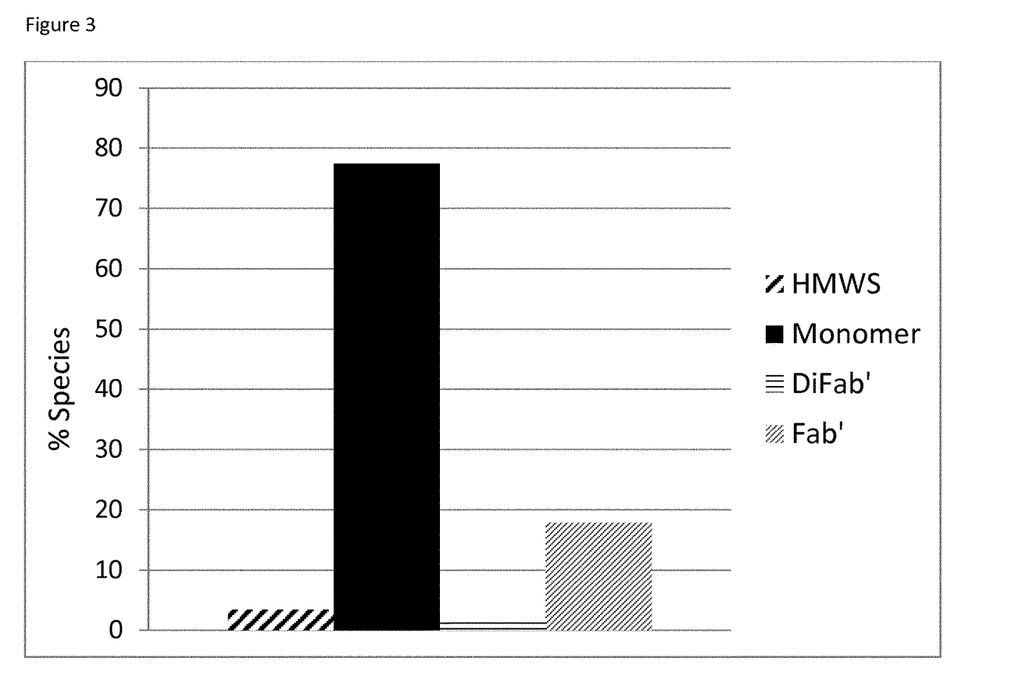
FIG. 3 shows the size exclusion HPLC analysis of the samples obtained from the PEGylation reaction of Fab'1 recovered from an E. coli periplasmic extract and purified according to a prior art method. HMWS refers to the amount of high molecular weight species or aggregates, monomer refers to the amount of Fab'1 coupled to PEG, diFab' refers to the amount of Fab'1 dimers, and Fab' refers to the amount of remaining unbound Fab'1.

PEGylation efficiency as determined using size exclusion HPLC resulted in a 77.4% Fab'1-PEG monomer (FIG. 3).

The invention claimed is:

1. A method for manufacturing an antigen-binding fragment of an antibody coupled to a polyethylene glycol (PEG) molecule, comprising:
   a) culturing prokaryotic host cells under conditions such that the cells express the antigen-binding fragment of an antibody,
   b) purifying said antigen-binding fragment from a mixture containing the host cells and other contaminants, wherein said purification comprises at least two chromatography steps and wherein a reducing agent is added to said mixture and the antigen-binding fragment is maintained in the presence of said reducing agent from the first chromatography step until the last chromatography step,
   c) adding PEG to the purified antigen-binding fragment and coupling the PEG to a cysteine in the hinge region of said antigen-binding fragment, and
   d) recovering said antigen-binding fragment coupled to PEG.

2. The method according to claim 1, wherein the reducing agent is selected from glutathione, β-mercaptoethanol, β-mercaptoethylamine, dithiothreitol, Tris(2-carboxyethyl)phosphine, cysteine, and combinations thereof.

3. The method according to claim 2, wherein the reducing agent is 0.1 mM to 100 mM glutathione.

4. The method according to claim 1, wherein the reducing agent is removed from the recovered antigen binding fragment.

5. The method according to claim 1, said method comprising the expression of the antigen-binding fragment into the periplasmic space of a Gram negative prokaryotic cell and release of the antigen-binding fragment from the periplasmic space of the Gram negative prokaryotic cell prior to the step of protein purification.

6. The method according to claim 5, wherein said protein extraction step is performed in the presence of a reducing agent.

7. The method according to claim 3, wherein the reducing agent is 0.5 mM to 2 mM glutathione.

8. The method according to claim 6, wherein the reducing agent is 0.1 mM to 100 mM glutathione.

9. The method according to claim 1, wherein said antigen binding fragment is a Fab'.

10. The method according to claim 1, wherein said cysteine in said antigen binding fragment is in the antibody hinge.

11. The method according to claim 8, wherein the reducing agent is 0.5 mM to 2 mM glutathione.

12. The method according to claim 1, wherein said PEG molecule is 40,000 PEG-maleimide.

* * * * *

UNITED STATES PATENT AND TRADEMARK OFFICE
CERTIFICATE OF CORRECTION

| | |
|---|---|
| PATENT NO. | : 10,626,143 B2 |
| APPLICATION NO. | : 15/538282 |
| DATED | : April 21, 2020 |
| INVENTOR(S) | : Christopher Mark Illidge and Neil Alan Watson |

Page 1 of 1

It is certified that error appears in the above-identified patent and that said Letters Patent is hereby corrected as shown below:

In the Specification

<u>Column 19,</u>
Lines 39-40, "eluted with a 50 with 50 mM" should read --eluted with 50 mM--.

Signed and Sealed this
Twenty-fifth Day of August, 2020

Andrei Iancu
*Director of the United States Patent and Trademark Office*